United States Patent [19]
Chim et al.

[11] Patent Number: 5,873,366
[45] Date of Patent: Feb. 23, 1999

[54] METHOD FOR TRANSMYOCARDIAL REVASCULARIZATION

[76] Inventors: Nicholas Chim; Marilyn M. Chou, both of 900 Alice St., Oakland, Calif. 94607

[21] Appl. No.: 744,397

[22] Filed: Nov. 7, 1996

[51] Int. Cl.⁶ ............................................. A61N 5/06
[52] U.S. Cl. .............................. 128/898; 606/15
[58] Field of Search ................. 606/7, 12, 14–15, 606/19, 194; 604/4, 27, 53; 435/1.1, 1.2; 514/275; 128/898

[56] References Cited

U.S. PATENT DOCUMENTS

| | | | |
|---|---|---|---|
| 4,658,817 | 4/1987 | Hardy | 128/303.1 |
| 5,125,924 | 6/1992 | Rudko | 606/12 |
| 5,125,926 | 6/1992 | Rudko | 606/19 |
| 5,380,316 | 1/1995 | Aita et al. | 606/7 |
| 5,389,096 | 2/1995 | Aita et al. | 606/15 |
| 5,428,039 | 6/1995 | Cohen | 514/275 |
| 5,554,152 | 9/1996 | Aita et al. | 606/7 |
| 5,554,497 | 9/1996 | Raymond | 435/1.2 |
| 5,607,421 | 3/1997 | Jeevanandam et al. | 606/15 |
| 5,695,457 | 12/1997 | St. Goar et al. | 604/4 |
| 5,755,687 | 5/1998 | Knudson et al. | 604/8 |

OTHER PUBLICATIONS

CardioGenesis Corporation, Percutaneous Myocardial Revascularization, Sep. 1995.
Dorros, G. and Cohn J. M., "Adenosine–Induced Transient Cardiac Asystole Enhances Precise Deployment of Stent–Grafts in the Thoracic or Abdominal Aorta" J Endovasc Surg, Aug. 1996.

Primary Examiner—Francis J. Jaworski
Attorney, Agent, or Firm—James J. Leary

[57] ABSTRACT

A method for performing transmyocardial revascularization (TMR) uses a cardioplegic agent to briefly stop the heartbeat long enough to create 10 to 40 carefully placed transmyocardial blood flow channels using a laser. The cardioplegic agent used may be adenosine or an adenosine triphosphate-sensitive potassium channel opener, such as aprikalim, or a standard hyperkalemic cardioplegic agent. The temporarily induced motionlessness of the heart allows accurate and efficient placement of the blood flow channels, while the short duration of the cardioplegic effect obviates the need for cardiopulmonary bypass. The blood flow channels can be formed from the exterior or the interior of the heart. Preferably, the TMR procedure is performed using an infrared laser, such as a $CO_2$ laser with an articulated-arm waveguide or a pulsed Nd:YAG laser with a flexible fiberoptic delivery system, or a near infrared laser, such as a holmium:YAG or erbium laser with a flexible fiberoptic delivery system, because of their ability to efficiently ablate clearly defined passages through myocardial tissue without inducing significant thermal damage to the surrounding myocardium. The laser delivery device or a separate probe can be used to verify the depth of the blood flow channels and their connection with the ventricular chamber. The heart resumes beating spontaneously after reperfusion, with no need for defibrillation or cardioversion. The TMR procedure can be performed by a cardiac or thoracic surgeon using standard open-chest surgical techniques or using a minimally invasive surgical approach or by an interventional cardiologist using a percutaneous transluminal intravascular approach.

22 Claims, 1 Drawing Sheet

METHOD FOR TRANSMYOCARDIAL REVASCULARIZATION

FIELD OF THE INVENTION

This invention relates generally to the surgical treatment of cardiovascular disease. More particularly, it relates to am improved method for performing laser transmyocardial revascularization.

BACKGROUND OF THE INVENTION

Transmyocardial revascularization is a recently developed addition to the armamentarium of treatments for cardiovascular disease. Previous approaches to treatment of cardiovascular disease have relied on two basic strategies: rerouting blood flow around blockages in the coronary arteries (coronary artery bypass grafting), and reducing or removing the atherosclerotic plaque causing a stenosis or occlusion in the coronary arteries (balloon angioplasty, laser angioplasty, and atherectomy). While some of these techniques have been extremely successful and have provided tremendous benefit to a great many patients, some patients remain untreatable using these approaches. Very elderly patients and patients who are weakened by very severe cardiovascular disease or other concurrent disease conditions and patients who have undergone previous coronary bypass surgery are considered to be bad surgical risks for coronary artery bypass grafting. Some other patients are not treatable using catheter approaches, such as balloon angioplasty, laser angioplasty, or atherectomy, because of diffuse arterial disease or extremely tortuous coronary arteries or recurrent restenosis.

Transmyocardial revascularization (TMR) offers an alternative approach to treatment of cardiovascular disease in which blood flow passages are artificially created through the myocardium directly from the interior of the ventricular chambers. The first attempts at transmyocardial revascularization were performed on animal models using a needle to create passages through the cardiac wall from the epicardium to the interior of the ventricular chambers. The puncture site in the epicardium would quickly seal over, leaving an open blood flow passage from the ventricular chambers into the myocardium. However, the patency of the blood flow channels created was short lived because the needle punctures through the myocardium would eventually heal over, closing off the blood flow passages within about two weeks after treatment. The next approach to transmyocardial revascularization involved the use of a surgical $CO_2$ laser to ablate blood flow passages from the exterior of the heart through the myocardium. This approach proved more successful because the laser-created blood flow passages through the myocardium did not heal over and therefore remained patent longterm. Perfusion studies, using radioactively labeled microspheres, demonstrated improved perfusion of the ischemic myocardium treated with TMR. A variation on this technique, described by Hardy in U.S. Pat. No. 4,658,817, uses a hollow needle to initially puncture the epicardium, then the laser energy is delivered through the needle lumen to ablate a passage through the myocardium into the ventricle. The theory behind this approach is that the needle punctures in the epicardium will heal quickly, while the laser-created blood flow passages through the myocardium will remain patent longterm. This patent and other U.S. patents referred to herein are hereby incorporated by reference in their entirety.

The disadvantage of these approaches to TMR is that the infrared beam of the surgical $CO_2$ laser, which was needed to effectively ablate the myocardial tissue, must be delivered through an articulated-arm waveguide using metal coated reflectors to direct the laser beam. The use of the articulated-arm waveguide necessitated that the TMR procedure be performed as open-chest surgery, which carried with it patient risk and trauma almost equivalent to standard coronary bypass surgery. The development of near infrared lasers, such as the holmium:YAG laser, which were effective for tissue ablation and which could be delivered through specialized fiberoptic devices, created opportunities for less invasive and therefore less traumatic approaches to TMR. U.S. Pat. No. 5,380,316 granted to Aita et al. describes a method for intra-operative myocardial device revascularization which uses a flexible fiberoptic device to deliver a beam from a holmium:YAG laser to the exterior of the heart through only a small incision in the chest wall. U.S. Pat. No. 5,389,096, also granted to Aita et al., describes a system and method for percutaneous myocardial revascularization which uses a flexible fiberoptic device to deliver a beam from a holmium:YAG laser to the interior wall of the heart through a percutaneous transluminal intravascular approach.

One of the major advantages of the TMR technique is that the procedure can be performed on a beating heart. This is significant because the second most important source of morbidity and complications during coronary bypass surgery, after the trauma of the median sternotomy to open the chest, is the cardiopulmonary bypass system, or heart-lung machine, which is used to support the circulatory system during extended periods of cardioplegic arrest. Operating on the beating heart eliminates many of the complications and risks of using the cardiopulmonary bypass system. However, using a laser on the beating heart carries with it a number of other inherent difficulties as well. One disadvantage of performing TMR on a beating heart is that it is difficult to verify whether the laser beam has fully penetrated the ventricular wall so that the practitioner can be sure that each blood flow channel makes a fluid connection with the interior of the ventricular chamber. The contraction of the heart muscle prevents accurate probing of the laser-created channels to verify complete penetration. In addition, at certain times during the cardiac cycle, the heart is particularly sensitive to the laser beam. For example, if the laser beam strikes the heart during the T portion of the electrocardiogram (ECG) wave, heart fibrillation can occur, which, if it is not corrected immediately by cardioversion or defibrillation, can lead to heart failure and death. To avoid this, Aita et al. recommend monitoring the heartbeat and gating the laser so that it generates one or two pulses during contractions of the ventricle (systole) and to generate no pulses during the rest of the heart cycle. U.S. Pat. No. 5,125,926 granted to Rudko et al. describes a system for synchronizing the laser pulses with the beat of the heart while performing TMR in order to avoid inducing fibrillation.

Synchronization is only a partial solution, however, because the motion of the cardiac wall due to the beating of the heart causes difficulties in positioning and focusing the laser device. Consequently, even with synchronization, only a fraction of the 15 to 30 laser pulses typically applied during TMR result in a patent blood flow passage from the ventricular chamber into the myocardium. The result of this is that it prolongs the procedure, it reduces the effective revascularization of the ischemic myocardium, and at the same time, it unnecessarily increases the laser-induced trauma to the heart. These problems would be minimized if the heart were stopped during the procedure, but, as discussed above, previous approaches to this have brought with them the problems inherent with cardiopulmonary bypass systems.

SUMMARY OF THE INVENTION

It would be desirable, therefore, to provide an improved method for performing transmyocardial revascularization which results in more accurate and efficient application of the laser energy so that a high percentage of the laser pulses result in a properly placed and patent blood flow channel connecting the endangered myocardium to the ventricular chamber. Such an improved method would increase the effective reperfusion of the ischemic myocardium and reduce the unnecessary trauma to the myocardium from misplaced laser pulses. To repeatedly achieve such accurate and efficient placement of the therapeutic laser pulses, it will be necessary to go beyond mere synchronization of the laser pulses with the heartbeat. It would, in fact, be desirable to temporarily stop the motion of the heart so that multiple laser pulses can be rapidly and accurately applied for optimum effect of the revascularization. At the same time, it is extremely important to avoid the complications and potential side effects that accompany the use of cardiopulmonary bypass, which would be needed for prolonged cessation of the heartbeat. It is desirable also to preserve the advantages of previously developed methods of performing TMR. For example, it is important to achieve longterm patency of the blood flow channels which are created, and it is important to avoid the danger of laser-induced fibrillation as a result of the procedure. It is also important to provide the options of performing TMR as a stand-alone procedure, using either a minimally invasive surgical approach or a percutaneous transluminal approach because of the reduced trauma to the patient, or as an adjunct to another procedure, such as balloon angioplasty or coronary artery bypass graft surgery.

To meet these needs, the present invention takes the form of a method for performing transmyocardial revascularization which uses a specialized cardioplegia technique to briefly stop the heartbeat just long enough for the laser to produce 10 to 40 carefully placed transmyocardial blood flow passages. Any approved pharmaceutical agent capable of producing a period of asystole from several seconds to several minutes may be used for the method. In one embodiment of the method, a bolus infusion of adenosine is used to produce a short period of ventricular asystole, up to about one minute duration. In a second embodiment of the method, a bolus infusion of an adenosine triphosphate-sensitive potassium channel opener, such as aprikalim, is used to produce a short period of hyperpolarized cardiac arrest. In a third embodiment of the method, a bolus infusion of a standard hyperkalemic cardioplegic agent is used to produce a short period of depolarized cardiac arrest. The temporarily induced motionlessness of the heart allows for accurate and efficient placement of the laser pulses, while the short duration of the cardioplegic effect obviates the need for cardiopulmonary bypass. Because the myocardium is not contracting during the period of asystole, the laser-created blood flow channels can be probed with the laser delivery device or with a separate instrument to verify sufficient penetration of the channels into the ventricular wall and the fluid connection between the blood flow channels and the ventricular chamber. The heart and the rest of the circulatory system tolerates the short periods of asystole induced by the cardioplegia technique very well without the need for cardiopulmonary support. The heart generally returns to normal sinus rhythm spontaneously after reperfusion, with no need for defibrillation or cardioversion.

Any laser or other device capable of ablating blood flow passages through the myocardium can be used for practicing the method of the present invention. In the currently preferred embodiment of the invention, the transmyocardial revascularization procedure is performed using an infrared or near infrared laser because of their ability to efficiently ablate clearly defined passages through myocardial tissue without inducing significant thermal damage to the surrounding myocardium. When there is direct access to the heart, for instance when using an open-chest approach or a minimally invasive direct approach, an infrared $CO_2$ surgical laser with an articulated-arm waveguide may be used for performing the TMR procedure. When a port-access surgical approach or a percutaneous transluminal approach is used for the TMR procedure, an infrared laser, such as a pulsed Nd:YAG laser, or a near infrared laser, such as a holmium:YAG or erbium laser, with a flexible fiberoptic delivery system may be used. Alternatively, the method may be performed using an ultraviolet excimer laser or other known laser devices.

DETAILED DESCRIPTION OF THE INVENTION

Figure 1:
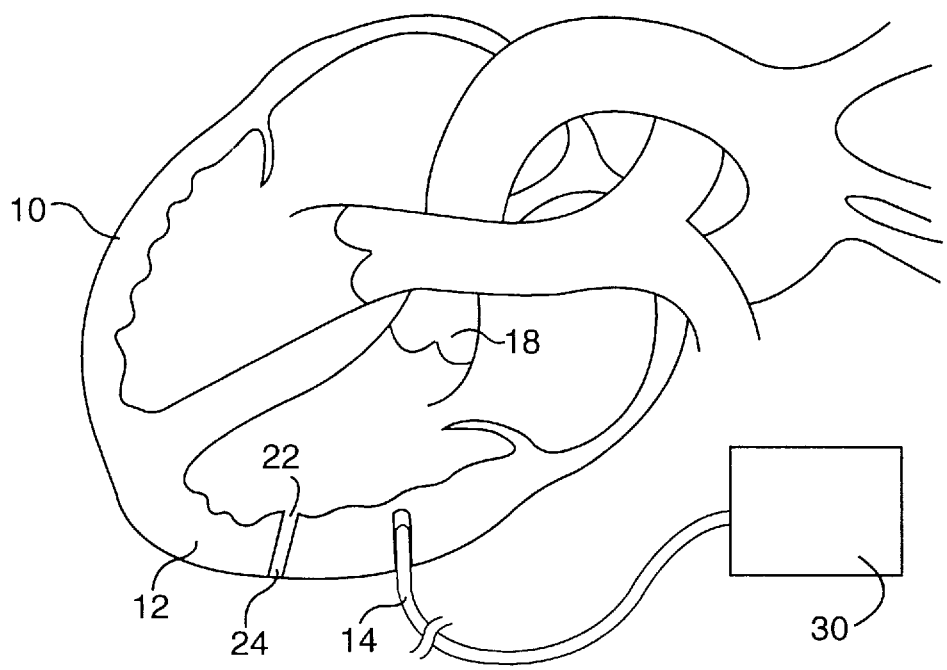
FIG. 1 is a schematic representation of the method for performing transmyocardial revascularization using a minimally invasive surgical approach to the ventricular wall.

The method of the present invention for performing transmyocardial revascularization is devised so that it can be performed by a cardiac or thoracic surgeon using standard open-chest surgical techniques or using the more recently developed minimally invasive direct surgical approach or the port-access surgical approach. Alternatively, the method can be performed by an interventional cardiologist using a percutaneous transluminal intravascular approach. The method may be practiced using any laser or other device capable of creating blood flow passages through the myocardium. It is preferable to use a device which can ablate a clean and clearly defined channel though the myocardial tissue and the endocardium, but that leaves the epicardium relatively intact so that there is little or no bleeding from the epicardium. It is important that the blood flow passages created by the device remain patent over the longterm and that any damage created in the epicardium is able to heal. It is also important that, while creating the channel, the device does not create significant thermal or mechanical damage in the surrounding tissue. In the currently preferred embodiment of the invention, the transmyocardial revascularization procedure is performed using an infrared or near infrared laser because of their ability to efficiently ablate clearly defined passages through myocardial tissue without inducing significant thermal damage to the surrounding myocardium. An infrared $CO_2$ surgical laser with an articulated-arm waveguide may be used for performing the TMR procedure when there is direct access to the heart, for instance when using an open-chest approach or a minimally invasive direct approach. An infrared laser, such as a pulsed Nd:YAG laser, or a near infrared laser, such as a holmium:YAG or erbium laser, with a flexible fiberoptic delivery system may be used for performing the TMR procedure when using a port-access surgical approach, a percutaneous transluminal approach or a direct surgical approach. The laser delivery device should focus the laser energy into a narrow beam to create a clearly defined channel approximately 1 mm wide through the myocardium to a depth of approximately 10–20 mm. When using an articulated-arm waveguide, the beam can be focused using a concave focusing mirror or a sapphire focusing lens. When using a flexible fiberoptic delivery device, it has been found that appropriate focusing is provided by a 300–600 micron diameter single fiber with an approximately hemispherical, flame-polished distal end. A separate focusing lens may also be used, particularly if a multiple fiber optical cable is used instead of a single fiber device. Alternatively, the method may be performed using an ultraviolet excimer laser or other known laser device.

The chosen laser device 30 should be prepared and tested according to the manufacturer's instructions. Then, using the chosen surgical or interventional technique, the operator gains access to the heart. A surgical approach is shown schematically in FIG. 1. After surgical access to the heart is established using open-chest or minimally invasive techniques, the pericardium is incised and opened over the left ventricle 12 of the heart 10. The laser delivery device 14 is positioned near the exterior of the left ventricle 12. An interventional approach is shown schematically in FIG. 2. A guiding catheter 16 or similar device is inserted via percutaneous access or an arterial cutdown and advanced into the aortic root 18. A flexible fiberoptic delivery device 20 is advanced through the guiding catheter 16 and carefully pushed across the aortic valve and positioned near the interior wall of the left ventricle 12.

The next step of the procedure involves establishing cardioplegia by administering a bolus of the chosen cardioplegic agent into the left and right coronary arteries. If an open-chest approach is used, the aortic root 18 or the individual left and right coronary arteries can be cannulated in the usual way for delivering the bolus of the cardioplegic agent. When using minimally invasive or intravascular techniques, a cardioplegia delivery catheter such as described in U.S. Pat. No. RE 35,352, granted to Peters, may be used, or the left and right coronary arteries may be individually intubated using catheters delivered via percutaneous access or an arterial cutdown. A third alternative, is to deliver a bolus of cardioplegic solution in a retrograde fashion, using a catheter and method such as described in U.S. Pat. No. 5,021,045, granted to Buckberg, et al. or U.S. Pat. No. 5,558,644, granted to Boyd, et al.

In one embodiment of the method, a bolus infusion of adenosine is administered at a dosage of approximately 0.15–0.25 mg/kg to produce a short period of ventricular asystole. Adenosine has a short half life of approximately 10 seconds so its effects are short acting, providing several seconds to about 20 seconds of asystole. In a second embodiment of the method, a bolus infusion of an adenosine triphosphate-sensitive potassium channel opener, such as aprikalim, is used to produce a short period of hyperpolarized cardiac arrest. This approach has the advantage that the heart is stopped in a hyperpolarized state, which is the natural resting state of the heart. This may provide improved myocardial protection compared to standard cardioplegic techniques. In a third embodiment of the method, a bolus infusion of a standard hyperkalemic cardioplegic agent is used to produce a short period of depolarized cardiac arrest. In this embodiment, the cardioplegic fluid preferably consists of an aqueous KCl solution mixed with oxygenated blood at a ratio of four parts blood to one part KCl solution. The aqueous KCl solution consists of crystalloid KCl mixed with saline to have a concentration in the range of 10–50 mEq $K^+$/liter, preferably 15–30 mEq $K^+$/liter. Alternatively, an aqueous KCl solution with a concentration in the range of 10–30 mEq $K^+$/liter, without a blood component, may be used. The cardioplegic fluid may be delivered as warm cardioplegia or as cold cardioplegia for improved myocardial protection. Cardioplegic arrest occurs almost immediate when the cardioplegic solution is infused. Using the second or third embodiments of the method, if desired, asystole can be maintained for an extended period using a continued drip of cardioplegic agent.

Figure 2:
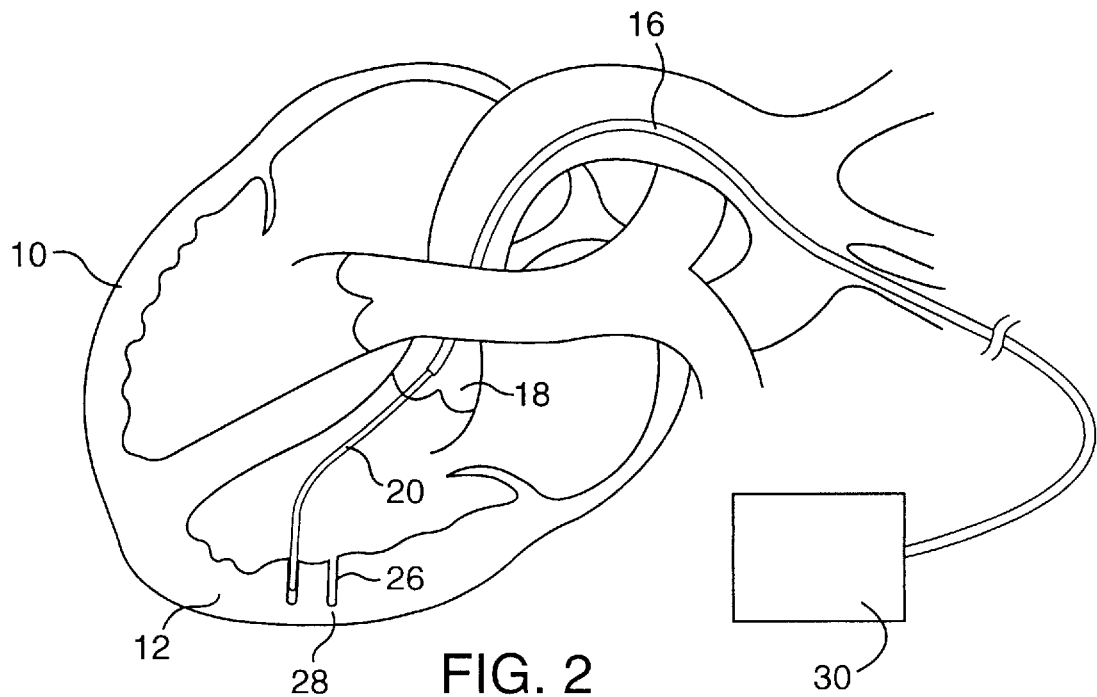
FIG. 2 is a schematic representation of the method for performing transmyocardial revascularization using a percutaneous transluminal intravascular approach.

While the heart is in asystole, a series of 10–40 blood flow channels approximately 1 mm in diameter are created through the myocardium in the ischemic portion of the ventricular wall using the laser delivery device. The laser parameters may be varied to achieve effective penetration through the myocardium according to clinical experience or future research. The following parameters are given by way of example to provide an enabling description. When using an infrared $CO_2$ surgical laser with an articulated-arm waveguide, approximately 50 J of laser energy is applied in 50 ms pulses until the laser has fully penetrated the ventricular wall. When using a pulsed Nd:YAG laser, 0.2–5 J of laser energy per pulse is delivered with a pulse width of approximately 50–600 microseconds at a pulse rate up to approximately 100 pulses per second. When using a near infrared holmium:YAG laser, 0.2–5 J of laser energy per pulse is delivered at a pulse rate of approximately 10–50 pulses per second. The blood flow channels can be created from the exterior of the heart or the interior of the heart. When creating the blood flow channels 22 from the exterior of the heart 10, as shown in FIG. 1, the laser delivery device 14 must fully penetrate through the ventricular wall 12, which may be 10–20 mm thick. Each of the blood flow channels 22 can be probed with the laser delivery device 14 while creating the channel to verify complete penetration of the channels 22 through the ventricular wall 12 and the fluid connection between the blood flow channels and the ventricular chamber. Alternatively, each of the channels 22 can be probed with a separate instrument after the channel has been formed. Because the myocardium is not contracting during the period of asystole, there is little friction to interfere with the tactile feedback of the probe which facilitates accurate probing and verification of each of the blood flow channels 22. After the blood flow channels 22 are formed, the exterior extremity 24 of the channel 22 quickly clots over to prevent excessive bleeding from the epicardium. When creating the blood flow channels 26 from the interior of the heart 10, as shown in FIG. 2, the laser delivery device 20 preferably penetrates only part-way through the ventricular wall 12, leaving the epicardium 28 intact. Because the myocardium is not contracting during the period of asystole, the depth of the blood flow channels 26 can be quickly and accurately verified by probing each one with the laser delivery device 20 while creating the channel. Alternatively, each of the channels 26 can be probed with a separate instrument after the channels been formed. Because the wall 12 of the heart 10 will be temporarily motionless, the blood flow channels can be quickly and efficiently created with careful attention to the placement of the channels. Because the heart is not beating there no need to synchronize the laser pulses with the heartbeat or the ECG signal, and because the heart is electrically quiet during asystole, there is essentially no danger of causing laser induced fibrillation or other arrhythmias. After the desired period of asystole, ranging from a few seconds to a few minutes, the heart is allowed to reperfuse with oxygenated blood and it resumes beating spontaneously. Generally, the heart will return to normal sinus rhythm spontaneously, with no need for defibrillation or cardioversion. If the heartbeat does not resume naturally or if fibrillation occurs, a shock can be delivered internally or externally to synchronize the heart chambers into their natural rhythm.

One period of cardioplegia should be sufficient to create all of the blood flow channels needed, particularly if the ischemic areas of the ventricular wall have been well mapped out beforehand for proper placement of the channels. It is envisioned that with specialized laser delivery devices or automated positioning and firing of the laser device, all of the blood flow channels needed can be regularly created in only one or two periods of cardioplegia. However, if more channels are, needed, a second bolus of cardioplegic agent can be administered after a sufficient refractory period to begin a second or third period of asystole. The heart and the rest of the circulatory system tolerates these short periods of asystole very well without the need for cardiopulmonary support. However, if desired, a femoral-to-femoral cardiopulmonary bypass system or a blood flow assist device, such as the Hemopump, may be used to augment circulatory blood flow. For high risk patients or patients whose cardiac function is already highly compromised, a blood flow assist device may be necessary.

In an alternative method, the heart rate can be slowed down without actually stopping the heart by administering a bolus of a heart slowing medication, such as a 10–20 ml bolus of esmolol 10–20. With the heart rate slowed down to approximately 30 beats per minute, approximately twice as many blood flow channels can be created per cardiac cycle with lower risk of laser induced fibrillation. This alternative method may also be used in conjunction with the cardioplegia method described above. With the heart rate slowed down before induction of cardioplegia, the oxygen demand of the heart muscle will be reduced, resulting in improved myocardial protection.

What is claimed is:

1. A method of performing transmyocardial revascularization on heart comprising the steps of:
   (a) temporarily stopping the heart from beating by inducing a brief period of asystole with a duration of less than approximately one minute;
   (b) creating at least one blood flow channel within a wall of the heart during said brief period of asystole, said at least one blood flow channel having a fluid connection with a chamber of the heart; and
   (c) allowing the heart to resume beating.

2. The method of claim 1 wherein step (a) comprises infusing the heart with a cardioplegic agent having a short half life to induce a brief period of asystole with a duration of less than approximately one minute.

3. The method of claim 2 wherein said brief period of asystole has a duration of less than approximately twenty seconds.

4. The method of claim 2 wherein said brief period of asystole is induced by a bolus infusion of adenosine at a concentration sufficient to induce asystole in the heart.

5. The method of claim 4 wherein said brief period of asystole is induced by a bolus infusion of adenosine at a dosage of approximately 0.15–0.25 mg/kg.

6. The method of claim 2 further comprising the step of:
   (d) probing said at least one blood flow channel during said period of asystole to verify the fluid connection between said at least one blood flow channel and the chamber of the heart.

7. The method of claim 1 wherein steps (a), (b) and (c) are performed without cardiopulmonary bypass.

8. The method of claim 1 wherein step (b) comprises creating a multiplicity of blood flow channels within the wall of the heart.

9. The method of claim 1 wherein step (b) comprises irradiating an exterior surface of the heart with laser energy to create said at least one blood flow channel within the wall of the heart.

10. The method of claim 1 wherein step (b) comprises irradiating an interior surface of the heart with laser energy to create said at least one blood flow channel within the wall of the heart.

11. The method of claim 1 wherein step (b) comprises irradiating a surface of the heart with laser energy delivered through a fiberoptic laser delivery device to create said at least one blood flow channel within the wall of the heart.

12. The method of claim 1 wherein step (b) comprises irradiating a surface of the heart with infrared laser energy to create said at least one blood flow channel within the wall of the heart.

13. The method of claim 12 wherein step (b) further comprises generating said infrared laser energy with a $CO_2$ laser.

14. The method of claim 1 wherein step (b) comprises irradiating a surface of the heart with near-infrared laser energy to create said at least one blood flow channel within the wall of the heart.

15. The method of claim 14 wherein step (b) further comprises generating said near-infrared laser energy with a holmium:YAG laser.

16. The method of claim 1 wherein step (c) comprises reperfusing the heart with oxygenated blood to induce the heart to resume beating.

17. A method of performing transmyocardial revascularization on a heart comprising the steps of:
   (a) temporarily stopping the heart from beating by infusing the heart with a cardioplegic agent having a short half life to induce a brief period of asystole which has a duration of less than approximately one minute;
   (b) creating a multiplicity of blood flow channels within a wall of the heart by irradiating a surface of the heart with laser energy during said period of asystole, said blood flow channels having a fluid connection with a chamber of the heart; and
   (c) reperfusing the heart with oxygenated blood to induce the heart to resume beating.

18. The method of claim 17 wherein said brief period of asystole is induced by a bolus infusion of adenosine at a concentration sufficient to induce asystole in the heart.

19. The method of claim 18 wherein said brief period of asystole is induced by a bolus infusion of adenosine at a dosage of approximately 0.15–0.25 mg/kg.

20. The method of claim 17 further comprising the step of:
   (d) probing said blood flow channels during said period of asystole to verify the fluid connection between said blood flow channels and the chamber of the heart.

21. The method of claim 17 wherein said brief period of asystole has a duration of less than approximately twenty seconds.

22. The method of claim 18 wherein steps (a), (b) and (c) are performed without cardiopulmonary bypass.

* * * * *